United States Patent [19]

Ferber et al.

[11] Patent Number: 4,616,210

[45] Date of Patent: Oct. 7, 1986

[54] SPECTROPHOTOMETERS

[75] Inventors: Alan C. Ferber, Hillside; Morteza M. Chamran, deceased, late of Elmhurst, both of Ill., by Delories M. Chamran, legal representative

[73] Assignee: The Perkin-Elmer Corporation, Norwalk, Conn.

[21] Appl. No.: 651,188

[22] Filed: Sep. 14, 1984

[51] Int. Cl.[4] .......................... H03M 1/00; G01J 3/06
[52] U.S. Cl. .............................. 340/347 AD; 356/319; 356/325
[58] Field of Search ................ 340/347 AD; 356/319, 356/325, 326, 324, 323

[56] References Cited

U.S. PATENT DOCUMENTS

| | | | |
|---|---|---|---|
| 4,158,505 | 6/1979 | Mathisen et al. | 356/323 |
| 4,180,327 | 12/1979 | Maeda et al. | 356/325 |
| 4,238,830 | 12/1980 | Unvala | 356/325 |
| 4,279,510 | 7/1981 | Brown | 356/326 |
| 4,310,243 | 1/1982 | Brown et al. | 356/323 |

Primary Examiner—Bernard Roskoski
Attorney, Agent, or Firm—E. T. Grimes; F. L. Masselle

[57] ABSTRACT

In a spectrophotometer having an optical beam chopped into dark and light segments, a computer controlled system is described for determining background signal due to stray light, photomultiplier dark current, offsets of photometric amplifiers and other components, and the like and for subtracting this background signal from the overall signal so as to leave only the desired light measurement. The same computer system also sets the signal level automatically for highest resolution. Furthermore, the same computer acts as an analog to digital converter by successive approximation to supply the photometric signal to the microprocessor unit. Since the same components are involved in all these functions both analog and digital offsets of the components are automatically cancelled.

4 Claims, 4 Drawing Figures

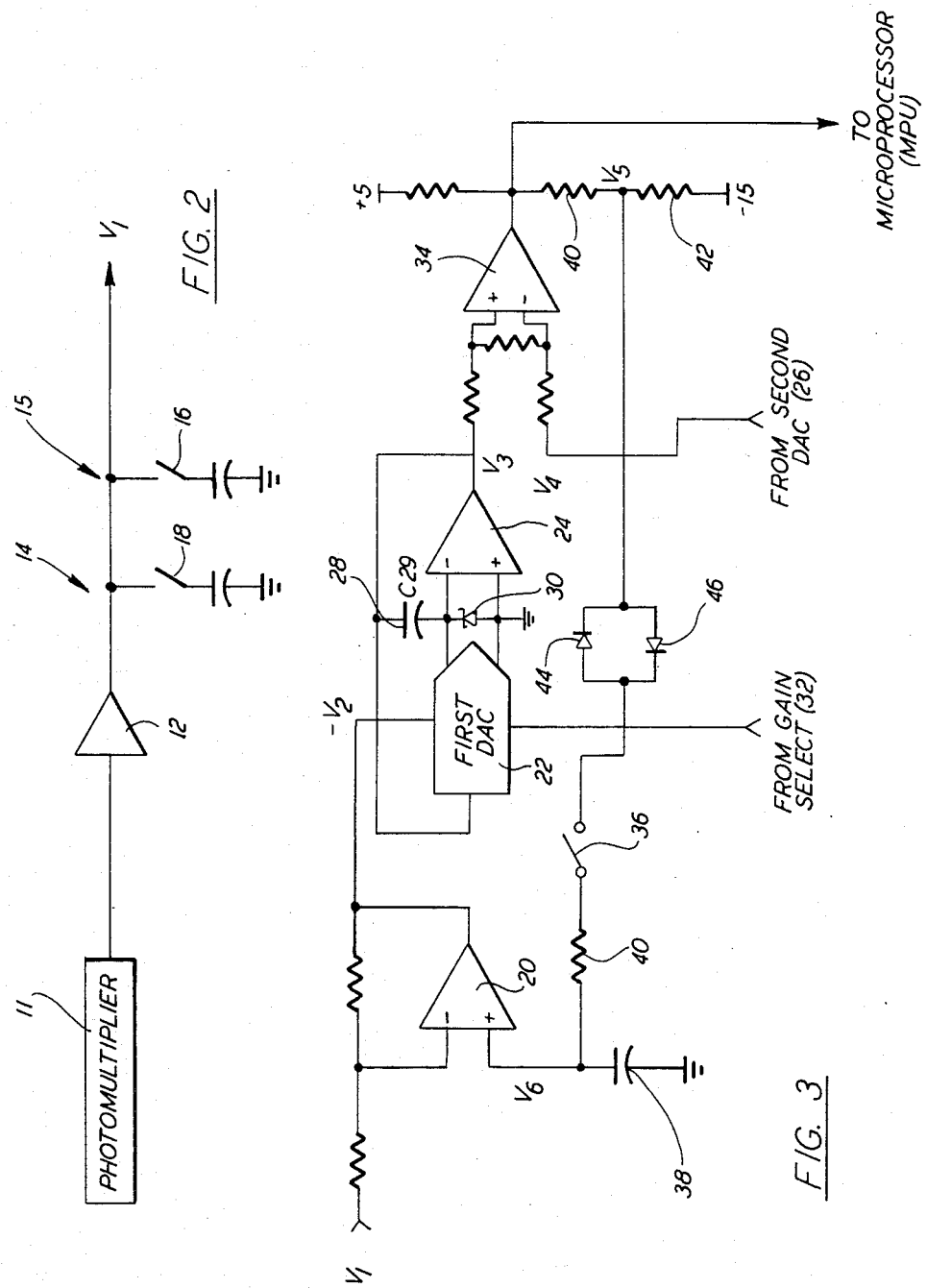

SPECTROPHOTOMETERS

BACKGROUND OF THE INVENTION

The photometric output of a spectrophotometer when appearing as an analog signal produced by a photomultiplier must be measured over a background signal containing such elements as photomultiplier dark current, preamplifier offset current and various currents due to thermal changes, stray light, etc. This background is determined by chopping the light beam passing through the spectrophotometer into dark and light segments. The background may then be determined during the dark period of each chopper cycle and subtracted from the total signal during the light period of each chopper cycle to leave the desired photometric signal.

Since the signals being measured may vary over a wide range it is desirable to incorporate a gain control means into the signal processor to maintain the signal level within a range which allows maximum resolution in the analog to digital conversion process used. By combining the background extraction with a subsequent gain controlled amplifier, not only the above cited background elements but also the offsets in the gain controlled amplifier and the analog to digital converter (ADC) can be eliminated automatically without adjustments.

It is an object of this invention to provide automatic gain control to provide the best analog to digital resolution.

It is a further object to provide automatic background correction for the photomultiplier dark current or any change therein due to temperature or excitation voltage or changes thereof.

It is an object to provide automatic background correction for the original offset voltages of the operational amplifiers and the ADC in the photometric circuit.

It is an object to provide automatic background correction for change in the above offset voltages due to temperature change.

It is a further object to provide automatic background correction for changes in the above due to gain changes in the photometric system.

BRIEF DESCRIPTION OF THE INVENTION

In the spectrophotometer of this invention, the photomultiplier output signal is preamplified by an operational amplifier and then stored by sample and hold circuits, one for the light, another for the dark part of the chopper cycle. These are alternately switched by the microprocessor unit (MPU) in step with the chopper cycle. The output voltage signal from the sample and hold circuits is passed through the auto-zero amplifier where a stored voltage representing the background signal is subtracted. Then the signal is applied to a gain selecting amplifier and then to a comparator and finally to the MPU. The comparator has several functions: to assist in gain selection; to generate the background signal voltage; and to effect the successive approximation analog to digital conversion of the light signal.

During an early part of the light section of the chopper cycle, the voltage output from the gain selecting amplifier is compared with limit voltages supplied from a microprocessor controlled second digital to analog converter (DAC). The gain is set according to this comparison. Then, by successive approximation under microprocessor control, the amplified light signal voltage is converted to a digital signal and sent to the microprocessor for data use.

During the dark part of the chopper cycle, the voltage output from the gain controlled amplifier is compared to a constant voltage from the second digital to analog converter and the comparator output is used to charge a capacitor with the background signal to be used as reference by the autozero amplifier.

It will be explained more fully hereinafter that the same components are used in all of the three functions cited above, their role in each being directed by the MPU.

BRIEF DESCRIPTION OF THE DRAWINGS

The foregoing and other objects, advantages and features of the present invention are described below in further detail in connection with the drawings which form a part of the disclosure wherein:

FIG. 2 is a circuit diagram showing the initial portion of the photometric circuit;

FIG. 3 is a circuit diagram of the portion of the photometric circuit relating to this invention.

DETAILED DESCRIPTION

Figure 1:
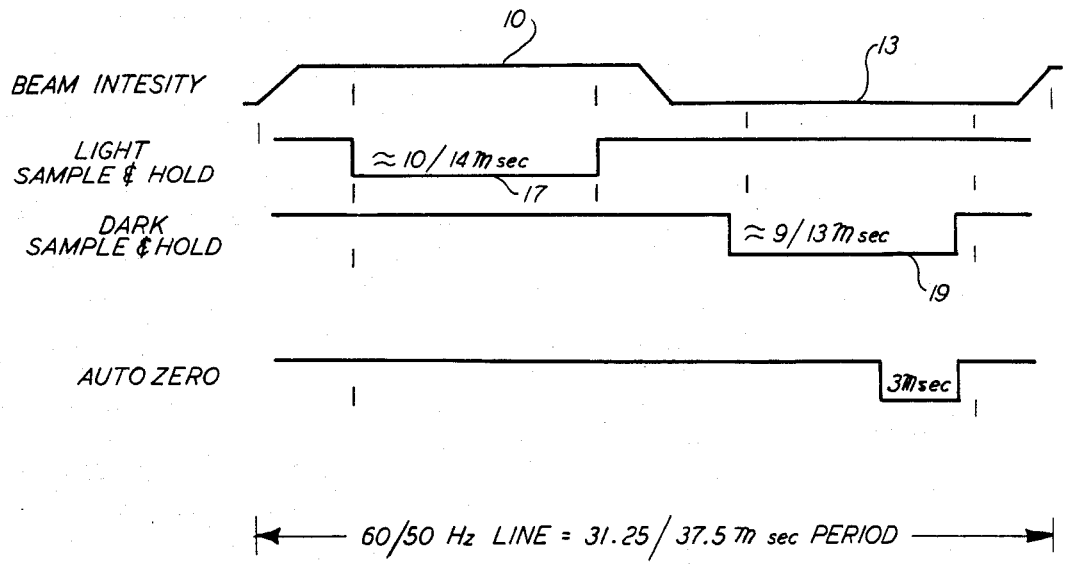
FIG. 1 is a graphic representation of the sample and hold timing chart.

Reference to FIG. 1 will make clear the timing relationships existing in the photometric system of the spectrophotometer, which is the presently preferred embodiment. The top line of FIG. 1 shows a beam intensity trace representing the chopped light signal at the output of the photomultiplier 11, FIG. 2. The high pulse indicated at 10 occurs during the light part of the chopper cycle and the low pulse indicated at 13 occurs during the dark part of the chopper cycle. Before this signal can be processed it must be amplified by a current to voltage converter or preamplifier 12, as illustrated in FIG. 2. This current to voltage converter raises the signal level high enough so that it may be operated on by sample and hold circuits indicated at 14 and 15, FIG. 2. These are storage circuits switched under control of the MPU and timed to correspond with the chopper timing as shown in the light sample and hold, and dark sample and hold, traces of FIG. 1. When the light sample and hold switch 16, FIG. 2, is closed a capacitor is charged with the voltage from the preamplifier 12 during the closure period. This voltage $V_1$ as indicated at 17, FIG. 1, during closure of the light sample and hold circuit 15, FIG. 2, is an analog measure of the light signal plus the background signal previously discussed. During closure of the switch 18 of the dark sample and hold circuit 14, $V_1$ is only the background signal as indicated at 19, FIG. 1.

Referring now to FIG. 3, $V_1$ is applied to the minus input of an operational amplifier 20, the "auto-zero" amplifier; concurrently a voltage $V_6$ is applied to the plus input. The voltage $V_6$ is applied to the plus input. The voltage $V_6$ is equivalent to the background signal; its derivation will be shown hereinafter. Under these circumstances the signal output of the auto-zero amplifier 20 will be $V_1$ less the background signal $V_6$. During closure of the light sample and hold circuit 15, therefore, this output signal, $-V_2$, represents only the desired photometric signal.

Figure 4:
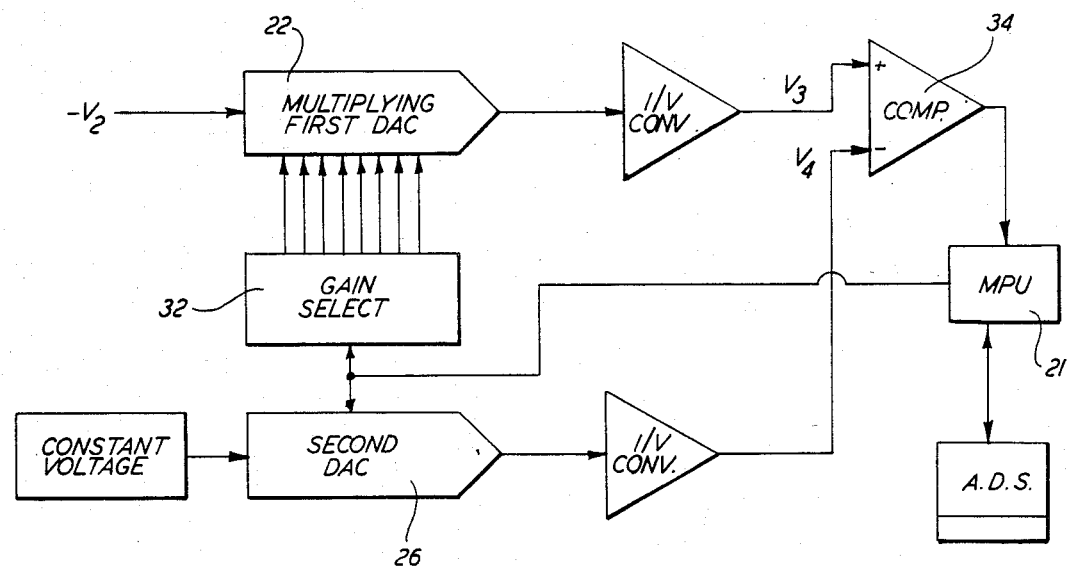
FIG. 4 is a block diagram showing the analog to digital and digital to analog conversion circuit elements.

The signal $-V_2$ is still in analog form and must be converted to a digital form before it can be handled by the MPU 21, FIG. 4. This is done by the well-known successive approximation method under the direction of the MPU. However, first the analog level of the signal must be adjusted to place it at a level most suitable for the successive approximation analog to digital conversion so as to achieve the highest resolution practical for the components to be used for this conversion. The analog level is adjusted by the gain selecting amplifier, which comprises a multiplying first DAC 22, tied into the feedback loop of an operational amplifier 24 so that the output voltage $V_3$ is $-V_2$ divided by a software selectable number less than unity. The gain of the amplifier will be controlled or selected during an early portion of the chopper light phase by comparing the voltage $V_3$ to limit voltages applied by the MPU controlled second DAC 26, FIG. 4. If $V_3$ falls below about one-half the full scale of the second DAC 26, the software increases the gain by a factor of two. If $V_3$ exceeds the approximate full scale of the second DAC 26, the gain is decreased by a factor of two. Capacitor 28, FIG. 3, is included in this gain controlled amplifier for stability, while diode 30 protects against start-up transients.

To better show the gain selection function and to clarify the successive approximation procedure, reference is now made to FIG. 4. The first DAC 22 is a 12 bit programmable gain switch with 8 of its 12 bits selectable via a gain select chip 32. This latter chip functions as an 8 bit clocked latch driver to select the multiplier factor of the first DAC 22. Bit 1 is the most significant bit and is gain "weighted" at $2^8$ or 256—on down to bit 8 which is the least significant bit with a gain "weighted" at $2^1$ or 2. With bits 1 through 8 simultaneously applied to the first DAC 22, the gain is slightly greater than $2^0$ or 1, $(1+1/256)$ which is software corrected to 1. Because of its circuit configuration, the gain scaling function of the first DAC is accomplished by dividing the analog signal $V_3$ by some software selected numerical value of less than unity. This is completed before successive approximation analog to digital conversion is carried out.

Due to the rapid data acquisition requirements of the preferred embodiment, successive approximation 12 bit analog to digital (A/D) conversion is next used. The 12 bit conversion rationale is to use the full scale voltage of the second DAC 26 as the base to extract 12 binary ratioed voltage "test" bits which are progressively compared, stored, summed, recompared, stored etc. against the currently processed analog signal voltage of unknown value. The two voltage levels are balanced (within the 12 bit resolution limitation of the second DAC 26) and the weighted summed binary test bits' voltage value is then assigned to the previously unknown analog signal voltage.

The processed analog signal $V_3$ is fed to the non-inverting input of comparator 34 and the second DAC reference signal $V_4$ is fed to its inverting input. The comparator 34 compares the known value reference voltage level $V_4$ to that of the unknown analog signal $V_3$. Only when the $V_4$ level exceeds the $V_3$ level will the comparator output cross over to zero volts, otherwise it will remain at $+5V$. If one-half of the full scale $V_4$ level exceeds the $V_3$ level the comparator output will go to zero, the second DAC and the MPU will each store a "0" bit and $V_4$ reference voltage level will be decreased to one-fourth full scale. The levels will again be compared and the "0" or "1" bit result stored. Each "1" bit is combined with the previous weighted sum of "1" bits to become the next $V_4$ level to be compared against the unknown $V_3$ level. This "compare", "store", "sum" process continues for the 12 bit (250 microsec.) duration, the final weighted summation of the 12 binary bits being equal to the analog signal value.

If, on the other hand, the unknown value $V_3$ level exceeds the one-half full scale $V_4$ level, the comparator output will remain positive, the second DAC and the MPU will each store a "1" bit and $V_4$ reference voltage level will be decreased to one-fourth full scale, the levels will again be compared and the "0" or "1" bit result stored. Each bit is combined with the previous weighted sum of "1" bits to become the next $V_4$ level to be compared against the unknown $V_3$ level. This "compare", "store", "sum" process continues for the 12 bit (250 μsec) duration, the final weighted summation of the 12 binary bits being equal to the analog signal value.

The role of the second DAC 26 in generating the background reference voltage $V_6$ will now be clarified. Referring to FIGS. 1 and 3, it will be seen that an auto-zero switch 36 is closed during the latter part of the dark period when $V_1$ has been stabilized by the dark sample and hold circuit 14, FIG. 2, previous to the auto-zero amplifier 20, FIG. 3. A constant reference voltage $V_4$ is then applied by the second DAC to the comparator 34. A negative feedback circuit is formed whereby voltage $V_5$ charges capacitor 38 via resistor 40 until the second DAC level and $V_3$ become equal. Actually, due to time delay effects, the comparator output is forced into oscillation. The 0 to $+5$ volt swings of the comparator are shifted by resistors 40 and 42 to approximately $-2$ to $+2$ volt swings. Diodes 44 and 46 serve to reduce changes in capacitor 38 when close to equilibrium. The resulting equilibrium voltage $V_6$ accurately represents the background level including all offsets in the described circuits. Furthermore, since the second DAC appears in both auto-zero and in gain selection and successive approximation functions the digital value corresponding to the second DAC reference level is subtracted from all results of analog to digital conversions.

While certain microprocessor controlled switching and logic functions have been here described whereby background cancellation and gain selection for best resolution are accomplished with a minimum of required components, it will be recognized that one skilled in the art, having appreciated the self compensating action of the arrangement of this invention, can substitute other equivalent components and routines to accomplish these several purposes while not departing from the spirit and scope of the invention as defined in the following claims.

What is claimed is:

1. A spectrophotometric system comprising, in combination:
   means for producing a photometric signal;
   optical chopper means for modulating said signal to produce a voltage alternating between a dark level and a light level;
   a sample and hold circuit for said dark level voltage signal;
   a sample and hold circuit for said light level voltage signal;
   auto-zero amplifier means;
   gain selecting amplifier means;
   comparator means;
   a microprocessor unit;

said microprocessor unit having control means for operating said spectrophotometric system in a dark signal mode wherein:
said auto-zero amplifier means receives said dark level voltage signal from said dark level sample and hold circuit and outputs a dark level signal;
said gain selecting amplifier means receives the output signal from said auto-zero amplifier means and outputs a dark level signal;
said comparator means including a digital to analog converter which receives control signals from said microprocessor unit and outputs a responsive constant voltage signal;
said comparator means receiving the output signal from said gain selecting amplifier means and compares it with said constant voltage signal to output a background signal voltage as a stored feedback to said auto-zero amplifier means;
said microprocessor unit having control means for operating said spectrophotometric system in a light signal mode wherein:
said auto-zero amplifier means receives a light level voltage signal from said light level sample and hold circuit and subtracts said background signal voltage to output a light level signal;
said gain selecting amplifier means receiving the output signal from said auto-zero amplifier means and incorporating a feed back gain factor to output a light level signal;
said digital to analog converter included in said comparator means receiving control signals from said microprocessor unit and outputting responsive limit voltages;
said comparator means receiving the light signal output from said gain selecting amplifier means and comparing it with said limit voltages to output a feedback gain control signal to said gain selecting amplifier means;
said comparator means including successive approximation means for analog to digital conversion which receives control signals from said microprocessor unit and light signals outputted from said gain selecting amplifier means to output digital signals to said microprocessor unit.

2. A spectrophotometric system according to claim 1 wherein each of said sample and hold circuits includes a capacitor and a switch.

3. A spectrophotometric system according to claim 1 wherein said auto-zero amplifier means includes an operational amplifier and a capacitor on which is stored a background voltage equivalent to the photometric analog measure of said background signal.

4. A spectrophotometric system according to claim 1 wherein said gain selecting amplifier means and said comparator means includes a programmable gain switch in combination with an operational amplifier, said combination being driven by a clocked latch driver from said digital to analog converter under said microprocessor unit control.

* * * * *